United States Patent
Busby et al.

(10) Patent No.: US 10,568,202 B2
(45) Date of Patent: Feb. 18, 2020

(54) TAMPER-RESPONDENT ASSEMBLY WITH INTERCONNECT CHARACTERISTIC(S) OBSCURING CIRCUIT LAYOUT

(71) Applicant: INTERNATIONAL BUSINESS MACHINES CORPORATION, Armonk, NY (US)

(72) Inventors: James A. Busby, New Paltz, NY (US); John R. Dangler, Rochester, MN (US); Michael J. Fisher, Poughkeepsie, NY (US); David C. Long, Wappingers Falls, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 281 days.

(21) Appl. No.: 15/658,717

(22) Filed: Jul. 25, 2017

(65) Prior Publication Data
US 2019/0037686 A1    Jan. 31, 2019

(51) Int. Cl.
*H05K 1/02*      (2006.01)
*H05K 1/11*      (2006.01)
(Continued)

(52) U.S. Cl.
CPC .......... *H05K 1/0275* (2013.01); *G01N 27/045* (2013.01); *G06F 21/87* (2013.01);
(Continued)

(58) Field of Classification Search
CPC ...... H05K 1/0275; H05K 1/115; H05K 1/181; H05K 1/0298; H05K 1/09; H05K 5/0208;
(Continued)

(56) References Cited

U.S. PATENT DOCUMENTS 5,202,591 A    4/1993   Walden
5,818,934 A    10/1998   Cuccia
(Continued)

OTHER PUBLICATIONS

Torrance, et al., "The State-of-the-Art in IC Reverse Engineering", Cryptographic Hardware and Embedded Systems, CHES 2009, Springer Berlin Heidelberg, 2009 (22 pages).
(Continued)

*Primary Examiner* — Melissa J Koval
*Assistant Examiner* — Rahul Maini
(74) *Attorney, Agent, or Firm* — Tihon Poltavets, Esq.; Kevin P. Radigan, Esq.; Heslin Rothenberg Farley & Mesiti P.C.

(57) ABSTRACT

Tamper-respondent assemblies and methods of fabrication are provided which include at least one tamper-respondent sensor and a detector. The at least one tamper-respondent sensor includes conductive lines which form, at least in part, at least one tamper-detect network of the tamper-respondent sensor(s). In addition, the tamper-respondent sensor(s) includes at least one interconnect element associated with one or more conductive lines of the conductive lines forming, at least in part, the tamper-detect network(s). The interconnect element(s) includes at least one interconnect characteristic selected to facilitate obscuring a circuit lay of the at least one tamper-detect network. In operation, the detector monitors the tamper-detect network(s) of the tamper-respondent sensor(s) for a tamper event.

6 Claims, 12 Drawing Sheets

(51) Int. Cl.
*H05K 1/18* (2006.01)
*H05K 5/02* (2006.01)
*G01N 27/04* (2006.01)
*G06F 21/87* (2013.01)
*H05K 1/09* (2006.01)

(52) U.S. Cl.
CPC .............. *H05K 1/115* (2013.01); *H05K 1/181* (2013.01); *H05K 5/0208* (2013.01); *H05K 1/09* (2013.01); *H05K 2201/10151* (2013.01); *H05K 2201/10204* (2013.01); *H05K 2201/10522* (2013.01)

(58) Field of Classification Search
CPC .......... H05K 2201/10151; H05K 2201/10204; H05K 2201/10371; H05K 2201/10522; G01N 27/045; G06F 21/86; G06F 21/87
USPC ......................................................... 324/693
See application file for complete search history.

(56) References Cited

U.S. PATENT DOCUMENTS

| | | | |
|---|---|---|---|
| 5,930,663 | A | 7/1999 | Baukus et al. |
| 6,294,816 | B1 | 9/2001 | Baukus et al. |
| 6,791,191 | B2 | 9/2004 | Chow et al. |
| 6,861,858 | B2 | 3/2005 | Chen et al. |
| 7,402,442 | B2 | 7/2008 | Condorelli et al. |
| 8,378,480 | B2 | 2/2013 | Chen et al. |
| 2007/0121575 | A1* | 5/2007 | Savry ................... G06K 19/073 370/351 |
| 2010/0031376 | A1* | 2/2010 | Bartley ................... G06F 21/87 726/34 |
| 2013/0021758 | A1* | 1/2013 | Bernstein ................ G06F 21/73 361/728 |
| 2014/0103286 | A1* | 4/2014 | Chu ........................ G06F 21/86 257/5 |
| 2016/0062418 | A1* | 3/2016 | Lewis ..................... H05K 1/09 361/679.31 |

OTHER PUBLICATIONS

Busby et al., "Tamper-Respondent Assembly with Interconnect Characteristic(s) Obscuring Circuit Layout", U.S. Appl. No. 15/810,295, filed Nov. 13, 2017 (pp. 1-48).

Busby et al., List of IBM Patents and/or Patent Applications Treated as Related, dated Nov. 13, 2017 (pp. 1-2).

Busby et al., "Tamper-Respondent Assembly with Interconnect Characteristic(s) Obscuring Circuit Layout", U.S. Appl. No. 16/596,941, filed Oct. 9, 2019 (52 pages).

Busby et al., "Replacement List of IBM Patents and/or Patent Applications Treated as Related", U.S. Appl. No. 15/658,717, filed Jul. 25, 2017, dated Oct. 10, 2019 (2 pages).

* cited by examiner

TAMPER-RESPONDENT ASSEMBLY WITH INTERCONNECT CHARACTERISTIC(S) OBSCURING CIRCUIT LAYOUT

BACKGROUND

Many activities require secure electronic communications. To facilitate secure electronic communications, an encryption/decryption system may be implemented on an electronic assembly or printed circuit board assembly that is included in equipment connected to a communications network. Such an electronic assembly is an enticing target for malefactors since it may contain codes or keys to decrypt intercepted messages, or to encode fraudulent messages. To prevent this, an electronic assembly may be mounted in an enclosure, which is then wrapped in a security sensor and encapsulated with polyurethane resin. A security sensor may be, in one or more embodiments, a web or sheet of insulating material with circuit elements, such as closely-spaced, conductive lines fabricated on it. The circuit elements are disrupted if the sensor is torn, and the tear can be sensed in order to generate an alarm signal. The alarm signal may be conveyed to a monitor circuit in order to reveal an attack on the integrity of the assembly. The alarm signal may also trigger an erasure of encryption/decryption keys stored within the electronic assembly.

SUMMARY

Provided herein, in one or more aspects, is a tamper-respondent assembly which includes: at least one tamper-respondent sensor including conductive lines forming, at least in part, at least one tamper-detect network of the at least one tamper-respondent sensor, and at least one interconnect element associated with one or more conductive lines of the conductive lines forming, at least in part, the at least one tamper-detect network. The at least one interconnect element includes at least one interconnect characteristic selected to facilitate obscuring a circuit layout of the at least one tamper-detect network. The tamper-respondent assembly further includes a detector to monitor the at least one tamper-detect network of the at least one tamper-respondent sensor for a tamper event.

In one or more other aspects, a tamper-respondent assembly is provided which includes: at least one electronic component; an enclosure surrounding, at least in part, the at least one electronic component; a tamper-respondent sensor associated with the enclosure and facilitating forming a secure volume about the at least one electronic component, and the detector. The tamper-respondent sensor includes: conductive lines forming, at least in part, at least one tamper-detect network of the tamper-respondent sensor; and at least one interconnect element associated with one or more conductive lines of the conductive lines forming, at least in part, the at least one tamper-detect network. The at least one interconnect element includes at least one interconnect characteristic selected to facilitate obscuring a circuit layout of the at least one tamper-detect network. The detector monitors the at least one tamper-detect network of the tamper-respondent sensor for a tamper event.

In one or more further aspects, a fabrication method is provided which includes fabricating a tamper-respondent assembly. The fabricating of the tamper-respondent assembly includes: providing at least one tamper-respondent sensor including conductive lines forming, at least in part, at least one tamper-detect network of the at least one tamper-respondent sensor, and at least one interconnect element associated with one or more conductive lines of the conductive lines forming, at least in part, the at least one tamper-detect network. The at least one interconnect element includes at least one interconnect characteristic selected to facilitate obscuring a circuit layout of the at least one tamper-detect network. In addition, fabricating the tamper-respondent assembly includes providing a detector to monitor the at least one tamper-detect network the at least one tamper-respondent sensor for a tamper event.

Additional features and advantages are realized through the techniques of the present invention. Other embodiments and aspects of the invention are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Aspects of the present invention and certain features, advantages, and details thereof, are explained more fully below with reference to the non-limiting example(s) illustrated in the accompanying drawings. Descriptions of well-known materials, fabrication tools, processing techniques, etc., are omitted so as not to unnecessarily obscure the invention in detail. It should be understood, however, that the detailed description and the specific example(s), while indicating aspects of the invention, are given by way of illustration only, and are not by way of limitation. Various substitutions, modifications, additions, and/or arrangements, within the spirit and/or scope of the underlying inventive concepts will be apparent to those skilled in the art for this disclosure. Note further that reference is made below to the drawings, which are not drawn to scale for ease of understanding, wherein the same reference numbers used throughout different figures designate the same or similar components. Also, note that numerous inventive aspects and features are disclosed herein, and unless otherwise inconsistent, each disclosed aspect or feature is combinable with any other disclosed aspect or feature as desired for a particular application, for instance, for establishing a secure volume about an electronic component(s) or electronic assembly to be protected.

Figure 1:
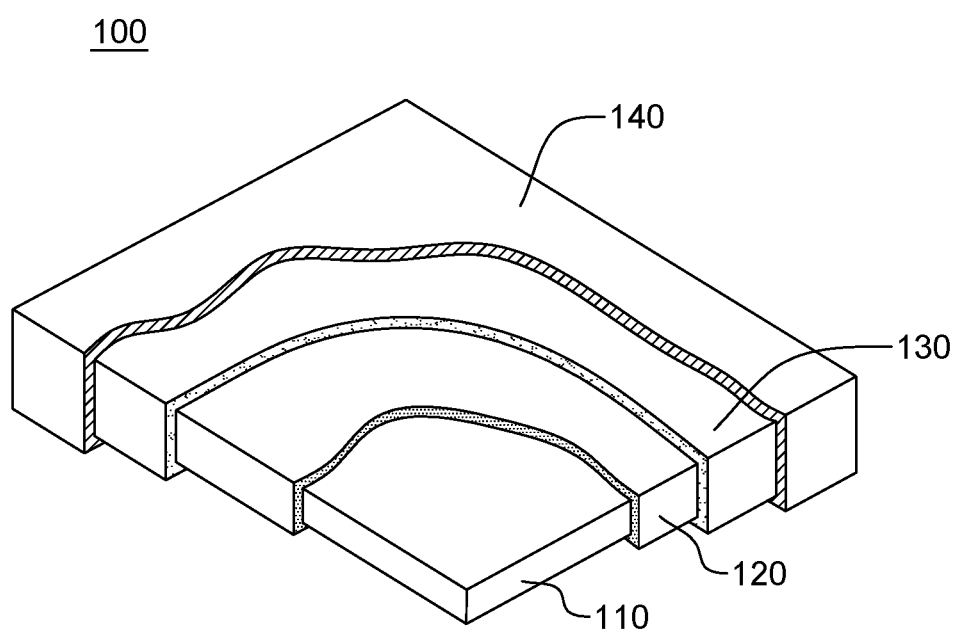
FIG. 1 is a partial cut-away of one embodiment of a tamper-proof electronic package, which may employ a tamper-respondent sensor, in accordance with one or more aspects of the present invention.

Reference is first made to FIG. 1, which illustrates one approach for an electronic package 100 configured as a tamper-proof electronic package for purposes of discussion. In the depicted embodiment, an electronic assembly enclosure 110 is provided containing, for instance, an electronic assembly, which in one embodiment may include a plurality of electronic components, such as an encryption and/or decryption module and associated memory. The encryption and/or decryption module may comprise security-sensitive information with, for instance, access to the information stored in the module requiring use of a variable key, and with the nature of the key being stored in the associated memory within the enclosure.

In one or more implementations, a tamper-proof electronic package or tamper-respondent assembly, such as depicted, is configured or arranged to detect attempts to tamper-with or penetrate into electronic assembly enclosure 110. Accordingly, electronic assembly enclosure 110 also includes, for instance, a monitor circuit which, if tampering is detected, activates an erase circuit to erase information stored within the associated memory, as well as the encryption and/or decryption module within the communications card. These components may be mounted on, and interconnected by, a multilayer circuit board, such as a printed circuit board or other multilayer substrate, and be internally or externally powered via a power supply provided within the electronic assembly enclosure.

In the embodiment illustrated, and as one example only, electronic assembly enclosure 110 may be surrounded by a tamper-respondent sensor 120, an encapsulant 130, and an outer, thermally conductive enclosure 140. In one or more implementations, tamper-respondent sensor 120 may include a tamper-respondent laminate that is folded around electronic assembly enclosure 110, and encapsulant 130 may be provided in the form of a molding. Tamper-respondent sensor 120 may include various detection layers, which are monitored through, for instance, a ribbon cable by the enclosure monitor, against attempts to penetrate enclosure 110 and damage the enclosure monitor or erase circuit, before information can be erased from the encryption module. The tamper-respondent sensor may be, for example, any such article commercially available or described in various publications and issued patents, or any enhanced article such as disclosed herein.

By way of example, tamper-respondent sensor 120 may be formed as a tamper-respondent laminate comprising a number of separate layers with, for instance, an outermost lamination-respondent layer including a matrix of, for example, diagonally-extending or sinusoidally-extending, conductive or semi-conductive lines printed onto a regular, thin insulating film. The matrix of lines forms a number of continuous conductors which would be broken if attempts are made to penetrate the film. The lines may be formed, for instance, by printing conductive traces onto the film and selectively connecting the lines on each side, by conductive vias, near the edges of the film. Connections between the lines and an enclosure monitor of the communications card may be provided via, for instance, one or more ribbon cables. The ribbon cable itself may be formed of lines of conductive material printed onto an extension of the film, if desired. Connections between the matrix and the ribbon cable may be made via connectors formed on one edge of the film. As noted, the laminate may be wrapped around the electronic assembly enclosure to define the tamper-respondent sensor 120 surrounding enclosure 110.

In one or more implementations, the various elements of the laminate may be adhered together and wrapped around enclosure 110, in a similar manner to gift-wrapping a parcel, to define the tamper-respondent sensor shape 120. The assembly may be placed in a mold which is then filled with, for instance, cold-pour polyurethane, and the polyurethane may be cured and hardened to form an encapsulant 130. The encapsulant may, in one or more embodiments, completely surround the tamper-respondent sensor 120 and enclosure 110, and thus form a complete environmental seal, protecting the interior of the enclosure. The hardened polyurethane is resilient and increases robustness of the electronic package in normal use. Outer, thermally conductive enclosure 140 may optionally be provided over encapsulant 130 to, for instance, provide further structural rigidity to the electronic package.

When considering tamper-proof packaging, the electronic package needs to maintain defined tamper-proof requirements, such as those set forth in the National Institutes of Standards and Technology (NIST) Publication FIPS 140-2, which is a U.S. Government Computer Security Standard, used to accredit cryptographic modules. The NIST FIPS 140-2 defines four levels of security, named Level 1 to Level 4, with Security Level 1 providing the lowest level of security, and Security Level 4 providing the highest level of security. At Security Level 4, physical security mechanisms are provided to establish a complete envelope of protection around the cryptographic module, with the intent of detecting and responding to any unauthorized attempt at physical access. Penetration of the cryptographic module enclosure from any direction has a very high probability of being detected, resulting in the immediate zeroization of all plain text critical security parameters (CSPs). Security Level 4 cryptographic modules are useful for operation in physically unprotected environments. Security Level 4 also protects a cryptographic module against a security compromise due to environmental conditions or fluctuations outside the module's normal operating ranges for voltage and temperature. Intentional excursions beyond the normal operating ranges may be used by an attacker to thwart the cryptographic module's defenses. The cryptographic module is required to either include specialized environmental protection features designed to detect fluctuations and zeroize, critical security parameters, or to undergo rigorous environmental failure testing to provide reasonable assurances that the module will not be affected by fluctuations outside the normal operating range in a manner than can compromise the security of the module.

To address the demands for ever-improving anti-intrusion technology, and the higher-performance encryption/decryption functions being provided, enhancements to the tamper-proof, tamper-evident packaging for the electronic component(s) or assembly at issue are desired.

Numerous enhancements are described herein to, for instance, tamper-proof electronic packages or tamper-respondent assemblies. The numerous inventive aspects described herein may be used singly, or in any desired combination. Additionally, in one or more implementations, the enhancements described herein may be provided to work within defined space limitations for existing packages.

Disclosed hereinbelow with reference to FIGS. 2A-11B are various approaches and/or enhancements to creating, for instance, a secure volume for accommodating one or more electronic components, such as one or more encryption and/or decryption modules and associated components of, for instance, a communications card or other electronic assembly to be protected.

Figure 2A:
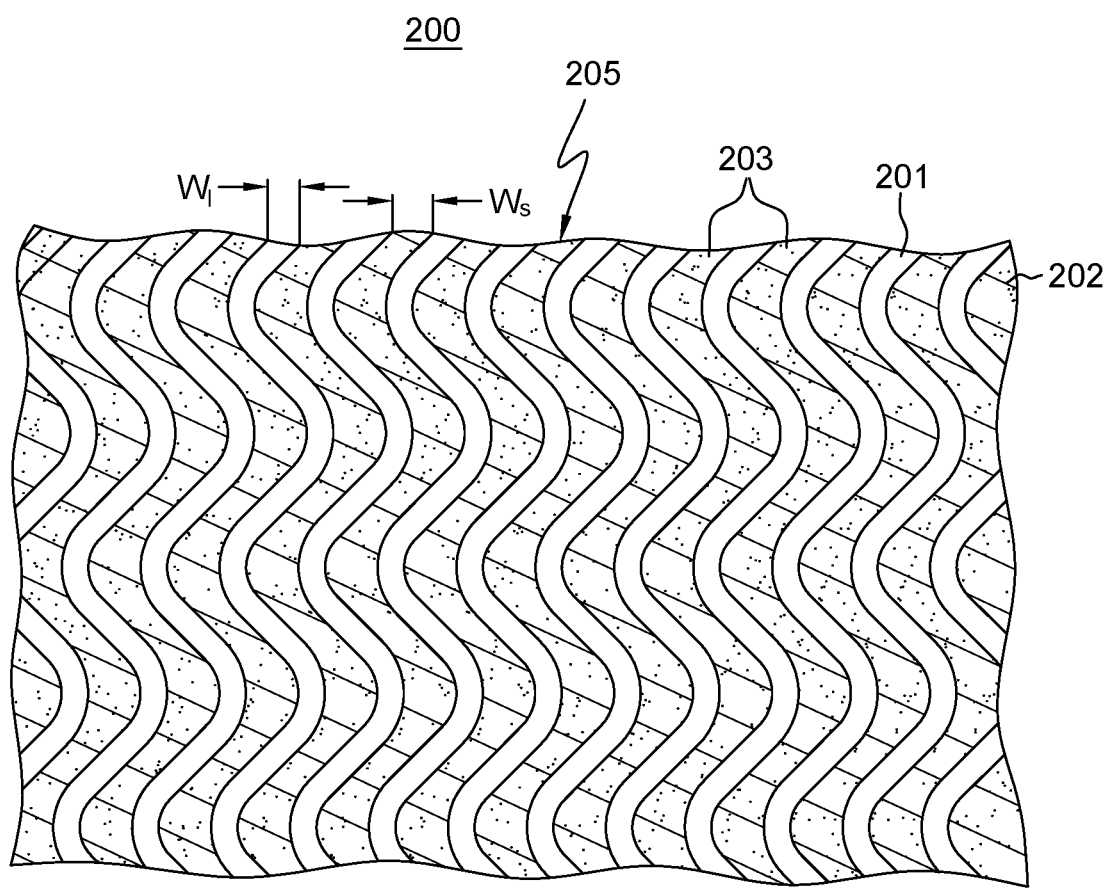
FIG. 2A depicts one embodiment of a tamper-respondent sensor with conductive lines forming, at least in part, at least one tamper-detect network, in accordance with one or more aspects of the present invention.
Figure 2B:
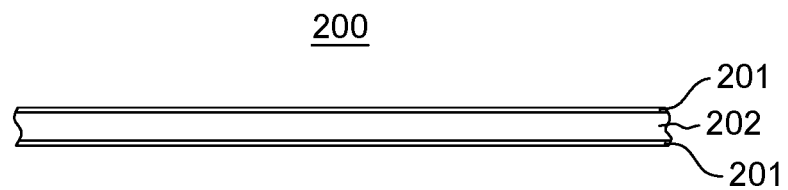
FIG. 2B is a cross-sectional elevational view of another embodiment of a tamper-respondent sensor, in accordance with one or more aspects of the present invention.

FIG. 2A depicts a portion of one embodiment of a tamper-respondent layer 205 (or laser and pierce-respondent layer) of a tamper-respondent sensor 200 or security sensor, such as discussed herein. In FIG. 2A, tamper-respondent layer 205 includes circuit lines or traces 201 provided on one or both opposite sides of a flexible layer 202, which in one or more embodiments, may be a flexible insulating layer or film. FIG. 2A illustrates circuit lines 201 on, for instance, one side of flexible layer 202, with the traces on the opposite side of the film being, for instance, the same pattern, but (in one or more embodiments) offset to lie directly below spaces 203, between circuit lines 201. As described below, the circuit lines on one side of the flexible layer may be of a line width $W_1$ and have a pitch or line-to-line spacing $W_s$ such that piercing of the layer 205 at any point results in damage to at least one of the circuit lines traces 201. In one or more implementations, the circuit lines may be electrically connected in-series or parallel to define one or more conductors which may be electrically connected in a network to an enclosure monitor, which may, in one or more implementations, monitor the resistance of the lines. Detection of an increase, or other change, in resistance, caused by cutting or damaging one of the traces, will cause information within the encryption and/or decryption module to be erased. Providing conductive lines 201 in a pattern, such as a sinusoidal pattern, may advantageously make it more difficult to breach tamper-respondent layer 205 without detection. Note, in this regard, that conductive lines 201 could be provided in any desired pattern. For instance, in an alternate implementation, conductive lines 201 could be provided as parallel, straight conductive lines, if desired, and the pattern or orientation of the pattern may vary between sides of a layer, and/or between layers.

As noted, as intrusion technology continues to evolve, anti-intrusion technology needs to continue to improve to stay ahead. In one or more implementations, the above-summarized tamper-respondent sensor 200 of FIG. 2A may be disposed over an outer surface of an electronic enclosure, such as an electronic enclosure described above in connection with FIG. 1. Alternatively, as described further herein, the tamper-respondent sensor may cover or line an inner surface of an electronic enclosure to provide a secure volume about at least one electronic component to be protected. Still further, the tamper-respondent sensor, or more particularly, the tamper-detect circuit(s) of the sensor, could be embedded within a multilayer circuit board such as described below.

In one or more aspects, disclosed herein is a tamper-respondent sensor 200 with circuit lines 201 having reduced line widths $W_1$ of, for instance, 200 µm, or less, such as less than or equal to 100 µm, or even more particularly, in the range of 30-70 µm. This is contrasted with conventional trace widths, which are typically on the order of 250 µm or larger. Commensurate with reducing the circuit line width $W_1$, line-to-line spacing width $W_s$ 203 is also reduced to less than or equal to 200 µm, such as less than or equal to 100 µm, or for instance, in a range of 30-70 µm. Advantageously, by reducing the line width $W_1$ and line-to-line spacing $W_s$ of circuit lines 201 within tamper-respondent sensor 200, the circuit line width and pitch is on the same order of magnitude as the smallest intrusion instruments currently available, and therefore, any intrusion attempt will necessarily remove a sufficient amount of a circuit line(s) to cause resistance to change, and thereby the tamper intrusion to be detected. Note that, by making the circuit line width of the smaller dimensions disclosed herein, any cutting or damage to the smaller-dimensioned circuit line will also be more likely to be detected, that is, due to a greater change in resistance. For instance, if an intrusion attempt cuts a 100 µm width line, it is more likely to reduce the line width sufficiently to detect the intrusion by a change in resistance. A change in a narrower line width is more likely to result in a detectable change in resistance, compared with, for instance, a 50% reduction in a more conventional line width of 350 µm to, for instance, 175 The smaller the conductive circuit line width becomes, the more likely that a tampering of that line will be detected.

Note also that a variety of materials may advantageously be employed to form the circuit lines when implemented using resistance monitoring. For instance, the circuit lines may be formed of a conductive ink (such as a carbon-loaded conductive ink) printed onto one or both opposite sides of one or more of the flexible layers 202 in a stack of such layers. Alternatively, a metal or metal alloy could be used to form the circuit lines, such as copper, silver, intrinsically conductive polymers, carbon ink, or nickel-phosphorus (NiP), or Omega-Ply®, offered by Omega Technologies, Inc. of Culver City, Calif. (USA), or Ticer™ offered by Ticer Technologies, Chandler, Ariz. (USA). Note that the process employed to form the fine circuit lines or traces on the order described herein is dependent, in part, on the choice of material used for the circuit lines. For instance, if copper circuit lines are being fabricated, then additive processing, such as plating up copper traces, or subtractive processing, such as etching away unwanted copper between trace lines, may be employed. By way of further example, if conductive ink is employed as the circuit line material, fine circuit lines on the order disclosed herein can be achieved by focusing on the rheological properties of the conductive ink formulation. Further, rather than simple pneumatics of pushing conductive ink through an aperture in a stencil with a squeegee, the screen emulsion may be characterized as very thin (for instance, 150 to 200 µm), and a squeegee angle may be used such that the ink is sheared to achieve conductive ink breakaway rather than pumping the conductive ink through the screen apertures. Note that the screen for fine line width printing such as described herein may have the following characteristics in one specific embodiment: a fine polyester thread for both warp and weave on the order of 75 micrometers; a thread count between 250-320 threads per inch; a mesh thickness of, for instance, 150 micrometers; an open area between threads that is at least 1.5× to 2.0× the conductive ink particle size; and to maintain dimensional stability of the print, the screen snap-off is kept to a minimum due the screen strain during squeegee passage.

In one or more implementations, circuit lines 201 of tamper-respondent sensor 200 are electrically connected to define one or more resistive networks. Further, the circuit lines may include one or more resistive circuit lines by selecting the line material, line width $W_1$ and line length $L_1$, to provide a desired resistance per line. As one example, a "resistive circuit line" as used herein may comprise a line with 1000 ohms resistance or greater, end-to-end. In one specific example, a circuit line width of 50 µm, with a circuit line thickness of 10 µm may be used, with the line length $L_1$ and material selected to achieve the desired resistance. At the dimensions described, good electrical conductors such as copper or silver may also be employed and still form a resistive network due to the fine dimensions noted. Alternatively, materials such as conductive ink or the above-noted OmegaPly® or Ticer™ may be used to define resistive circuit lines.

In a further aspect, the flexible layer 202 itself may be further reduced in thickness from a typical polyester layer by selecting a crystalline polymer to form the flexible layer or substrate. By way of example, the crystalline polymer could comprise polyvinylidene difluoride (PVDF), or Kapton, or other crystalline polymer material. Advantageously, use of a crystalline polymer as the substrate film may reduce thickness of the flexible layer 202 to, for instance, 2 mils thick from a more conventional amorphous polyester layer of, for instance, 5-6 mils. A crystalline polymer can be made much thinner, while still maintaining structural integrity of the flexible substrate, which advantageously allows for far more folding, and greater reliability of the sensor after folding. Note that the radius of any fold or curvature of the sensor is necessarily constrained by the thickness of the layers comprising the sensor. Thus, by reducing the flexible layer thickness to, for instance, 2 mils, then in a four tamper-respondent layer stack, the stack thickness can be reduced from, for instance, 20 mils in the case of a typical polyester film, to 10 mils or less with the use of crystalline polymer films.

As noted, the circuit lines 201 forming the at least one resistive network may be disposed on either the first side or the second side of the opposite sides of the flexible layer(s) 202 within the tamper-respondent sensor 200, or on both the first and second sides. One embodiment of this depicted in FIG. 2B, wherein circuit lines 201 are illustrated on both opposite sides of flexible layer 202. In this example, circuit lines 201 on the opposite sides of the tamper-respondent sensor 202 may each have line widths $W_1$ less than or equal to 200 µm, and those lines widths may be the same or different. Further, the line-to-line spacing width $W_s$ between adjacent lines of the circuit lines 201 may also be less than or equal to 200 µm, and may also be the same or different. In particular, the circuit lines may be different line widths on the two different sides of the tamper-respondent layer, and the line-to-line spacing widths may also be different. For instance, a first side of the tamper-respondent layer may have circuit line widths and line-to-line spacings of approximately 50 microns, while the second side of the tamper-respondent layer may have circuit lines and line-to-line spacing of 70 microns. Intrusion through the sensor is potentially made more difficult by providing such different widths. Circuit lines 201 on the opposite sides of the flexible layer 202 may also be in the same or different patterns, and in the same or different orientations. If in the same pattern, the circuit lines may be offset, as noted above, such that the circuit lines of one side align to spaces between circuit lines on the other side.

Figure 2C:
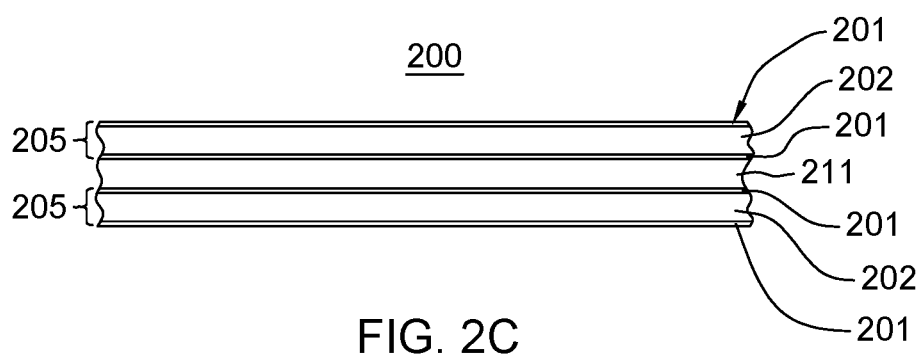
FIG. 2C is a cross-sectional elevational view of another embodiment of a tamper-respondent sensor, in accordance with one or more aspects of the present invention.

As illustrated in FIG. 2C, the tamper-respondent sensor 200 may comprise a stack of tamper-respondent layers 205 secured together via an adhesive 211, such as a double-sided adhesive film. The process may be repeated to achieve any desired number of tamper-respondent layers, or more particularly, any desired number of layers of circuit lines 201 within the tamper-respondent sensor to achieve a desired anti-intrusion sensor.

Figure 2D:
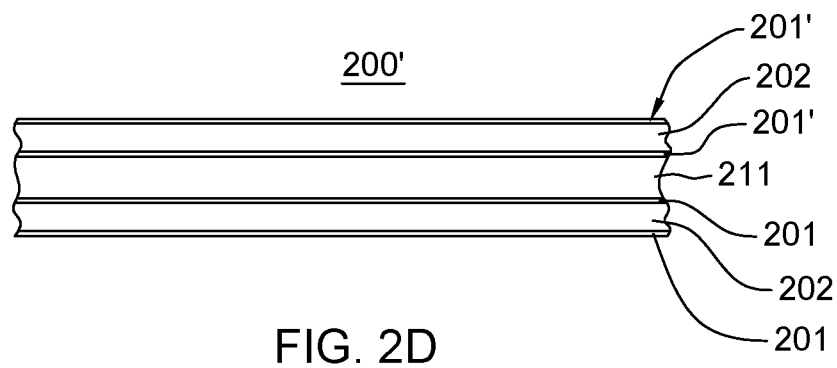
FIG. 2D is a cross-sectional elevational view of a further embodiment of a tamper-respondent sensor, in accordance with one or more aspects of the present invention.

An alternate tamper-respondent sensor 200' is depicted in FIG. 2D, where multiple flexible layers 202 with circuit lines are secured together via an adhesive 211, and by way of example, circuit lines are provided on one or both sides of each flexible layer. In this example, a first flexible layer 202 has first circuit lines 201 and a second flexible layer 202 has second circuit lines 201'. In one or more implementations the first circuit lines may have a first line width $W_1$ and the second circuit lines may have a second line width $W_1$, where the first line width of the first circuit lines 201 is different from the second line with the second circuit lines 201'. For instance, the first circuit line width may be 50 µm, and the second circuit line width may be 45 µm. Note that any desired combination of circuit line widths may be employed in this example, which assumes that the circuit line widths may be different between at least two of the layers. Additionally, the first circuit lines 201 of the first flexible layer may have first line-to-line spacing width $W_s$ and the second circuit lines 201' of second flexible layer may have a second line-to-line spacing width $W_s$, where the first line-to-line spacing width of the first circuit lines may be different from the second line-to-line spacing width of the second circuit lines. Note that this concept applies as well to circuit lines on only one side of flexible layer 202, where two or more of the flexible layers in the stack defining the tamper-respondent sensor may have different circuit line widths and/or different line-to-line spacing widths. This concept may be extended to any number of tamper-respondent layers within the tamper-respondent sensor to provide a desired degree of tamper protection.

In addition, or alternatively, the first circuit lines 201 of the first flexible layer may be formed of a first material, and the second circuit lines 201' of the second flexible layer may be formed of a second material, where the first material of the first circuit lines 201 may be different from the second material of the second circuit lines 201'. For instance, first circuit lines 201 may be formed of conductive ink, and second circuit lines 201' may be formed of a metal, such as copper. By providing tamper-respondent sensor 200' with at least some of the circuit lines formed of a metal material, such as copper, enhanced tamper detection may be obtained. For instance, an intrusion tool passing through one or more layers of circuit lines 201' formed of a metal could generate debris which may be distributed during the intrusion attempt and result in shorting or otherwise damaging one or more other tamper-respondent layers within the tamper-respondent sensor 200'. If desired, more than two materials may be employed in more than one layers of circuit lines within the tamper-respondent sensor.

Figure 3A:
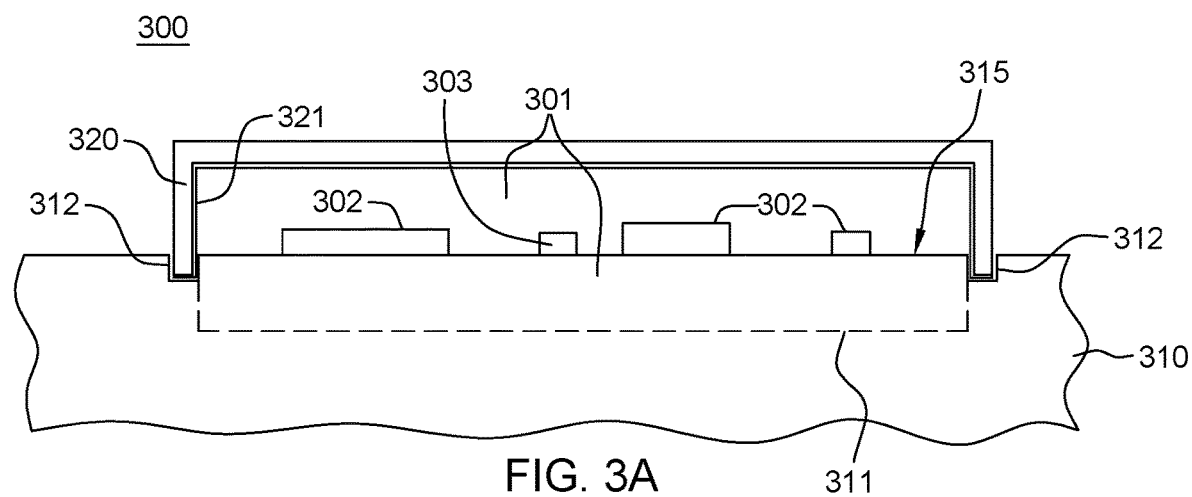
FIG. 3A is a cross-sectional elevational view of another embodiment of a tamper-proof electronic package, or tamper-respondent assembly, which includes (in part) an enclosure, and a multilayer circuit board with an embedded tamper-respondent sensor, in accordance with one or more aspects of the present invention.
Figure 3B:
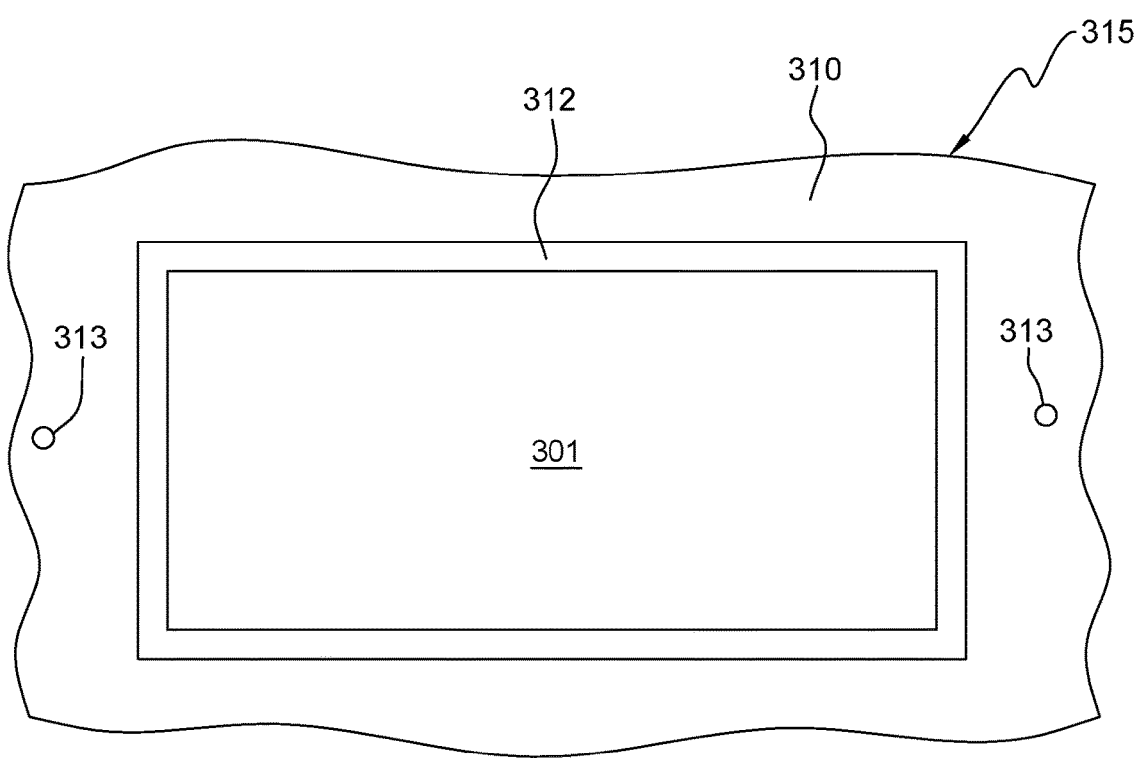
FIG. 3B is a top plan view of the multilayer circuit board of FIG. 3A, depicting one embodiment of the secure volume defined, in part, within the multilayer circuit board, in accordance with one or more aspects of the present invention.

FIGS. 3A & 3B depict another embodiment of a tamper-proof electronic package 300, or tamper-respondent assembly, which comprises one or more electronic components, such as a circuit 315 and/or electronic devices (or elements) 302 to be protected, in accordance with one or more further aspects of the present invention.

Referring collectively to FIGS. 3A & 3B, circuit 315 resides on or is embedded within a multilayer circuit board 310, which also has an embedded tamper-respondent sensor 311 that facilitates defining, in part, a secure volume 301 associated with multilayer circuit board 310 that (in one or more embodiments) extends into multilayer circuit board 310. In particular, in the embodiment of FIGS. 3A & 3B, secure volume 301 may exist partially within multilayer circuit board 310, and partially above multilayer circuit board 310. One or more electronic devices 302 are mounted to multilayer circuit board 310 within secure volume 301 and may comprise, for instance, one or more encryption modules and/or decryption modules, and/or associated components, to be protected within the tamper-proof electronic package. In one or more implementations, the one or more electronic components to be protected may comprise, for instance, a secure communications card of a computer system.

Tamper-proof electronic package 300 further includes an enclosure 320, such as a pedestal-type enclosure, mounted to multilayer circuit board 310 within, for instance, a continuous groove (or trench) 312 formed within an upper surface of multilayer circuit board 310, and secured to the multilayer circuit board 310 via, for instance, a structural adhesive disposed within continuous groove 312. In one or more embodiments, enclosure 320 may comprise a thermally conductive material and operate as a heat sink for facilitating cooling of the one or more electronic components 302 within the secure volume. A security mesh or tamper-respondent sensor 321 may be associated with enclosure 320, for example, wrapping around the inner surface of enclosure 320, to facilitate defining, in combination with tamper-respondent sensor 311 embedded within multilayer circuit board 310, secure volume 301. In one or more implementations, tamper-respondent sensor 321 may extend down into continuous groove 312 in multilayer circuit board 310 and may, for instance, even wrap partially or fully around the lower edge of enclosure 320 within continuous groove 312 to provide enhanced tamper detection where enclosure 320 couples to multilayer circuit board 310. In one or more implementations, enclosure 320 may be securely affixed to multilayer circuit board 310 using, for instance, a bonding material such as an epoxy or other adhesive.

Briefly described, tamper-respondent sensor 321 may comprise, in one or more examples, one or more tamper-respondent layers which include circuit lines or traces provided on one or both sides of a flexible layer, which in one or more implementations, may be a flexible insulating layer or film. The circuit lines on one or both sides of the flexible layer may be of a line width and have a pitch or line-to-line spacing such that piercing of the layer at any point results in damage to one or more of the circuit lines or traces. In one or more implementations, the circuit lines may define one or more conductors which may be electrically connected in a network to an enclosure monitor or detector 303, which monitors, for instance, resistance on the lines, or as described below, in the case of conductors, may monitor for a nonlinearity, or non-linear conductivity change, on the conductive lines. Detection of a change in resistance or a nonlinearity caused by cutting or damaging one or more of the lines, will cause information within the secure volume to be automatically erased. The conductive lines of the tamper-respondent sensor may be in any desired pattern, such as a sinusoidal pattern, to make it more difficult to breach the tamper-respondent layer without detection.

For resistive monitoring, a variety of materials may be employed to form the circuit lines. For instance, the circuit lines may be formed of a metal or metal alloy could be used to form the circuit lines, such as copper, silver, intrinsically-conductive polymers, carbon ink, or nickel phosphorous (NiP), or Omegaply®, offered by Omega Technologies, Inc., of Culver City, Calif. (USA), or Ticer™, offered by Ticer Technologies, Chandler, Ariz. (USA). The process employed to form the fine circuit lines or traces is dependent, in part, on the choice of materials used for the circuit lines. For instance, if copper circuit lines are fabricated, then additive processing, such as plating of copper traces, or subtractive processing, such as etching away unwanted copper between trace lines, may be employed.

As noted, in one or more implementations, the circuit lines of the tamper-respondent sensor(s) lining the inner surface(s) of enclosure 320, or even printed directly onto one or more layers formed over the inner surface of enclosure 320, may be connected to define one or more detect networks.

If a flexible layer is used over the inner surface of enclosure 320, then the flexible layer may be formed of a crystalline polymer material. For instance, the crystalline polymer could comprise polyvinylidene difluoride (PVDF), or Kapton, or other crystalline polymer material. Advantageously, a crystalline polymer may be made much thinner, while still maintaining structural integrity of the flexible substrate, which also allows for enhanced folding, and greater reliability of the sensor after folding.

As depicted in FIG. 3B, one or more external circuit connection vias 313 may be provided within multilayer circuit board 310 for electrically connecting to the one or more electronic components within secure volume 301. These one or more external circuit connection vias 313 may electrically connect to one or more external signal lines or planes (not shown) embedded within multilayer circuit board 310 and extending, for instance, into a secure base region of (or below) secure volume 301, as explained further below. Electrical connections to and from secure volume 301 may be provided by coupling to such external signal lines or planes within the multilayer circuit board 310.

As noted, secure volume 301 may be sized to house one or more electronic components to be protected, and may be constructed to extend into multilayer circuit board 310. In one or more implementations, multilayer circuit board 10 includes electrical interconnect within the secure volume 301 defined in the board, for instance, for electrically connecting one or more tamper-respondent layers of the embedded tamper-respondent sensor 311 to associated monitor circuitry also disposed within secure volume 301, along with, for instance, one or more daughter cards, such as memory DIMMs, PCIe cards, processor cards, etc.

Note that the packaging embodiment depicted in FIGS. 3A & 3B is presented by way of example only. Other configurations of enclosure 320, or multilayer circuit board 310 may be employed, and/or other approaches to coupling enclosure 320 and multilayer circuit board 310 may be used. For instance, in one or more alternate implementations, enclosure 320 may be securely affixed to an upper surface of multilayer circuit board 310 (without a continuous groove) using, for instance, a structural bonding material such as an epoxy or other adhesive.

Figure 4:
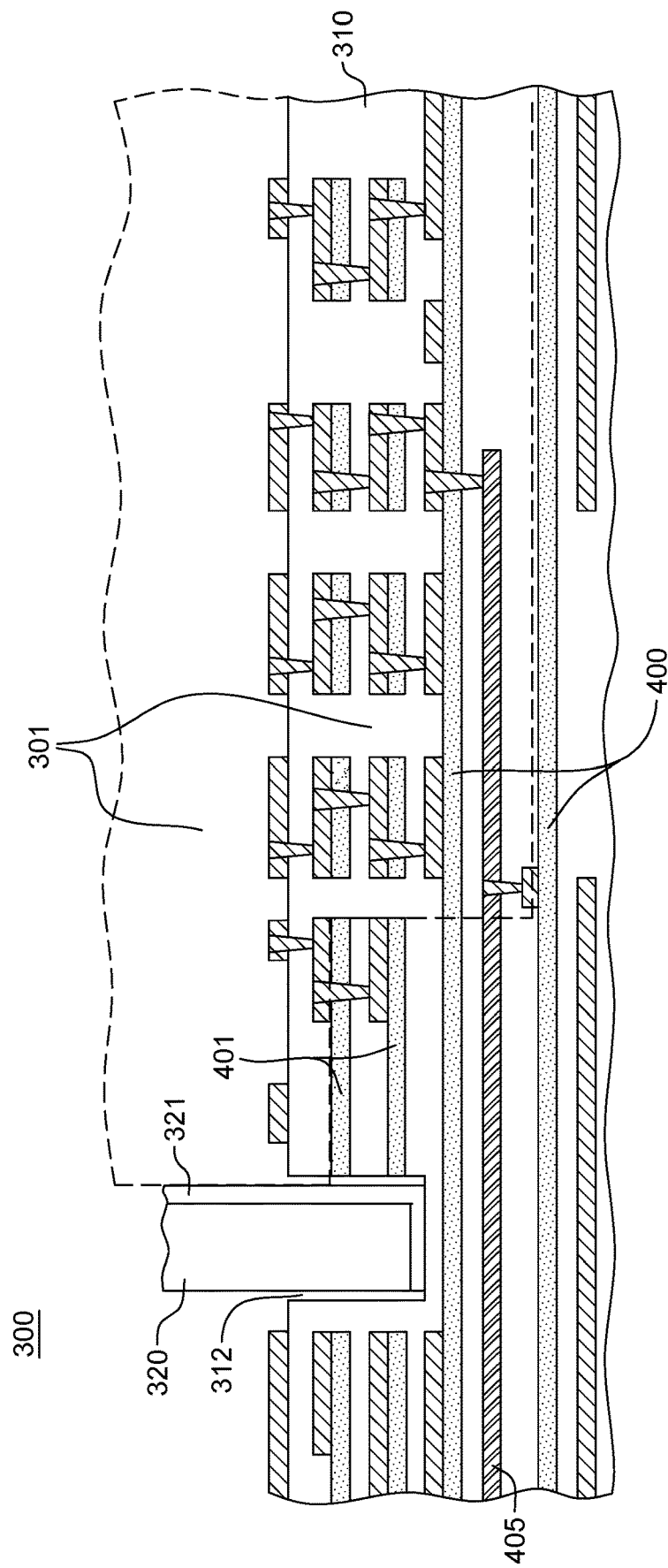
FIG. 4 is a partial cross-sectional elevational view of a more detailed embodiment of the tamper-respondent assembly of FIGS. 3A & 3B comprising (in part) an enclosure, and a multilayer circuit board with embedded tamper-respondent sensor, in accordance with one or more aspects of the present invention.

By way of further example, FIG. 4 depicts a partial cross-sectional elevational view of a more detailed embodiment of tamper-proof electronic package 300, and in particular, of multilayer circuit board 310, to which enclosure 320 is secured. In this configuration, the embedded tamper-respondent sensor includes multiple tamper-respondent layers including, by way of example, at least one tamper-respondent mat (or base) layer 400, and at least one tamper-respondent frame 401. In the example depicted, two tamper-respondent mat layers 400 and two tamper-respondent frames 401 are illustrated, by way of example only. The lower-most tamper-respondent mat layer 400 may be a continuous sense or detect layer extending completely below the secure volume being defined within and/or above multilayer circuit board 310. One or both tamper-respondent mat layers 400 below secure volume 301 may be partitioned into multiple circuit zones. Within each tamper-respondent mat layer, or more particularly, within each circuit zone of each tamper-respondent mat layer, multiple circuits or conductive traces may be provided in any desired configuration. Further, the conductive traces within the tamper-respondent layers may be implemented as, for instance, a resistive layer.

As illustrated, one or more external signal lines or planes 405 may enter secure volume 301 between, in one embodiment, two tamper-respondent mat layers 400, and then electrically connect upwards into the secure volume 301 through one or more conductive vias, arranged in any desired location and pattern. In the configuration depicted, the one or more tamper-respondent frames 401 are disposed at least inside of the area defined by continuous groove 312 accommodating the base of enclosure 320. Together with the tamper-respondent sensor(s) 321 associated with enclosure 320, tamper-respondent frames 301, and tamper-respondent mat layers 400, define secure volume 301, which may extend, in part, into multilayer circuit board 310. With secure volume 301 defined, in part, within multilayer circuit board 310, the external signal line(s) 405 may be securely electrically connected to, for instance, the one or more electronic components mounted to, or of, multilayer circuit board 310 within secure volume 301. In addition, secure volume 301 may accommodate electrical interconnection of the conductive traces of the multiple tamper-respondent layers 400, 301, for instance, via appropriate monitor circuitry.

Added security may be provided by extending tamper-respondent mat layers 400 (and if desired, tamper-respondent frames 401) outward past the periphery of enclosure 320. In this manner, a line of attack may be made more difficult at the interface between enclosure 320 and multilayer circuit board 310 since the attack would need to clear, for instance, tamper-respondent mat layers 400, the enclosure 320, as well as the tamper-respondent frames 401 of the embedded tamper-respondent sensor.

Numerous variations on multilayer circuit board 310 of FIGS. 3A-4 are possible. For instance, in one embodiment, the embedded tamper-respondent sensor may include one or more tamper-respondent mat layers 400 and one or more tamper-respondent frames 401, such as described above, and a tri-plate structure comprising one or more external signal lines or layers sandwiched between an upper ground plane and a lower ground plane. In this configuration, high-speed transfer of signals to and from the secure volume, and in particular, to and from the one or more electronic components resident within the secure volume, would be facilitated.

Note also that, once within the secure volume is defined in part within multilayer circuit board 310, conductive vias within the secure volume between layers of multilayer circuit board 310 may be either aligned, or offset, as desired, dependent upon the implementation. Alignment of conductive vias may facilitate, for instance, providing a shortest connection path, while offsetting conductive vias between layers may further enhance security of the tamper-proof electronic package by making an attack into the secure volume through or around one or more tamper-respondent layers of the multiple tamper-respondent layers more difficult.

The tamper-respondent layers of the embedded tamper-respondent sensor formed within the multilayer circuit board of the electronic circuit or electronic package may include multiple conductive traces or lines formed between, for instance, respective sets of input and output contacts or vias at the trace termination points. Any pattern and any number of conductive traces or circuits may be employed in defining a tamper-respondent layer or a tamper-respondent circuit zone within a tamper-respondent layer. For instance, 4, 6, 8, etc., conductive traces may be formed in parallel (or otherwise) within a given tamper-respondent layer or circuit zone between the respective sets of input and output contacts to those conductive traces.

Figure 5:
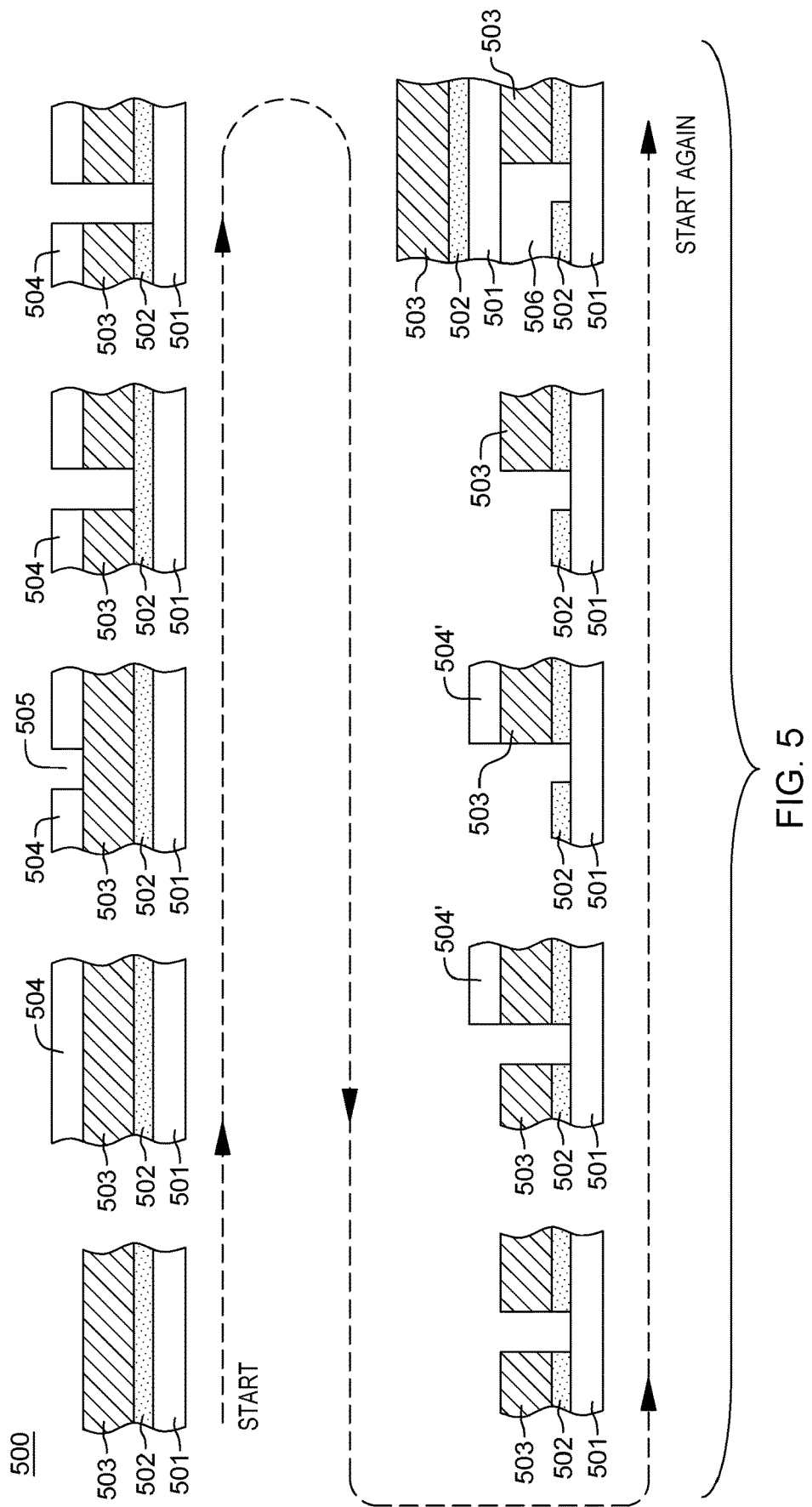
FIG. 5 depicts one embodiment of a process of fabricating a multilayer circuit board with an embedded tamper-respondent sensor, in accordance with one or more aspects of the present invention.

In one or more implementations, the multilayer circuit board may be a multilayer wiring board or printed circuit board formed, for instance, by building up the multiple layers of the board. FIG. 5 illustrates one embodiment for forming and patterning a tamper-respondent layer within such a multilayer circuit board.

As illustrated in FIG. 5, in one or more implementations, a tamper-respondent layer, such as a tamper-respondent mat layer or a tamper-respondent frame disclosed herein, may be formed by providing a material stack comprising, at least in part, a structural layer 501, such as a pre-preg (or pre-impregnated) material layer, a trace material layer 502 for use in defining the desired trace patterns, and an overlying conductive material layer 503, to be patterned to define conductive contacts or vias electrically connecting to the pattern of traces being formed within the trace material layer 502, for instance, at trace terminal points. In one or more implementations, the trace material layer 502 may comprise nickel phosphorous (NiP), and the overlying conductive layer 503 may comprise copper. Note that these materials are identified by way of example only, and that other trace and/or conductive materials may be used within the build-up 500.

A first photoresist 504 is provided over build-up 500, and patterned with one or more openings 505, through which the overlying conductive layer 503 may be etched. Depending on the materials employed, and the etch processes used, a second etch process may be desired to remove portions of trace material layer 502 to define the conductive traces of the subject tamper-respondent layer. First photoresist 504 may then be removed, and a second photoresist 504' is provided over the conductive layer 503 features to remain, such as the input and output contacts. Exposed portions of conductive layer 503 are then etched, and the second photoresist 504' may be removed, with any opening in the layer being filled, for instance, with an adhesive (or pre-preg) and a next build-up layer is provided, as shown. Note that in this implementation, most of overlying conductive layer 503 is etched away, with only the conductive contacts or vias remaining where desired, for instance, at the terminal points of the traces formed within the layer by the patterning of the trace material layer 502. Note that any of a variety of materials may be employed to form the conductive lines or traces within a tamper-respondent layer. Nickel-phosphorous (NiP) is particularly advantageous as a material since it is resistant to contact by solder, or use of a conductive adhesive to bond to it, making it harder to bridge from one circuit or trace to the next during an attempt to penetrate into the protected secure volume of the electronic circuit. Other materials which could be employed include OhmegaPly®, offered by Ohmega Technologies, Inc., of Culver City, Calif. (USA), or Ticer™, offered by Ticer Technologies of Chandler, Ariz. (USA).

The trace lines or circuits within the tamper-respondent layers, and in particular, the tamper-respondent circuit zones, of the embedded tamper-respondent sensor, along with the tamper-respondent detector monitoring the enclosure, may be electrically connected to detect or compare circuitry provided, for instance, within secure volume 301 (FIG. 3A) of the tamper-proof electronic package. The detect circuitry may include various bridge or compare circuits, and conventional printed wiring board electrical interconnect inside secure volume 301 (FIG. 3A), for instance, located within the secure volume defined by the tamper-respondent frames 401 (FIG. 4), and the tamper-respondent mat layers 400 (FIG. 4).

Note that advantageously, different tamper-respondent circuit zones on different tamper-respondent layers may be electrically interconnected into, for instance, the same detect circuitry. Thus, any of a large number of interconnect configurations may be possible. For instance, if each of two tamper-respondent mat layers contains 30 tamper-respondent circuit zones, and each of two tamper-respondent frames contains 4 tamper-respondent circuit zones, then, for instance, the resultant 68 tamper-respondent circuit zones may be connected in any configuration within the secure volume to create the desired arrangement of circuit networks within the secure volume being monitored for changes in resistance or tampering. Note in this regard, that the power supply or battery for the tamper-respondent sensor may be located internal or external to the secure volume, with the sensor being configured to trip and destroy any protected or critical data if the power supply or battery is tampered with.

Figure 6:
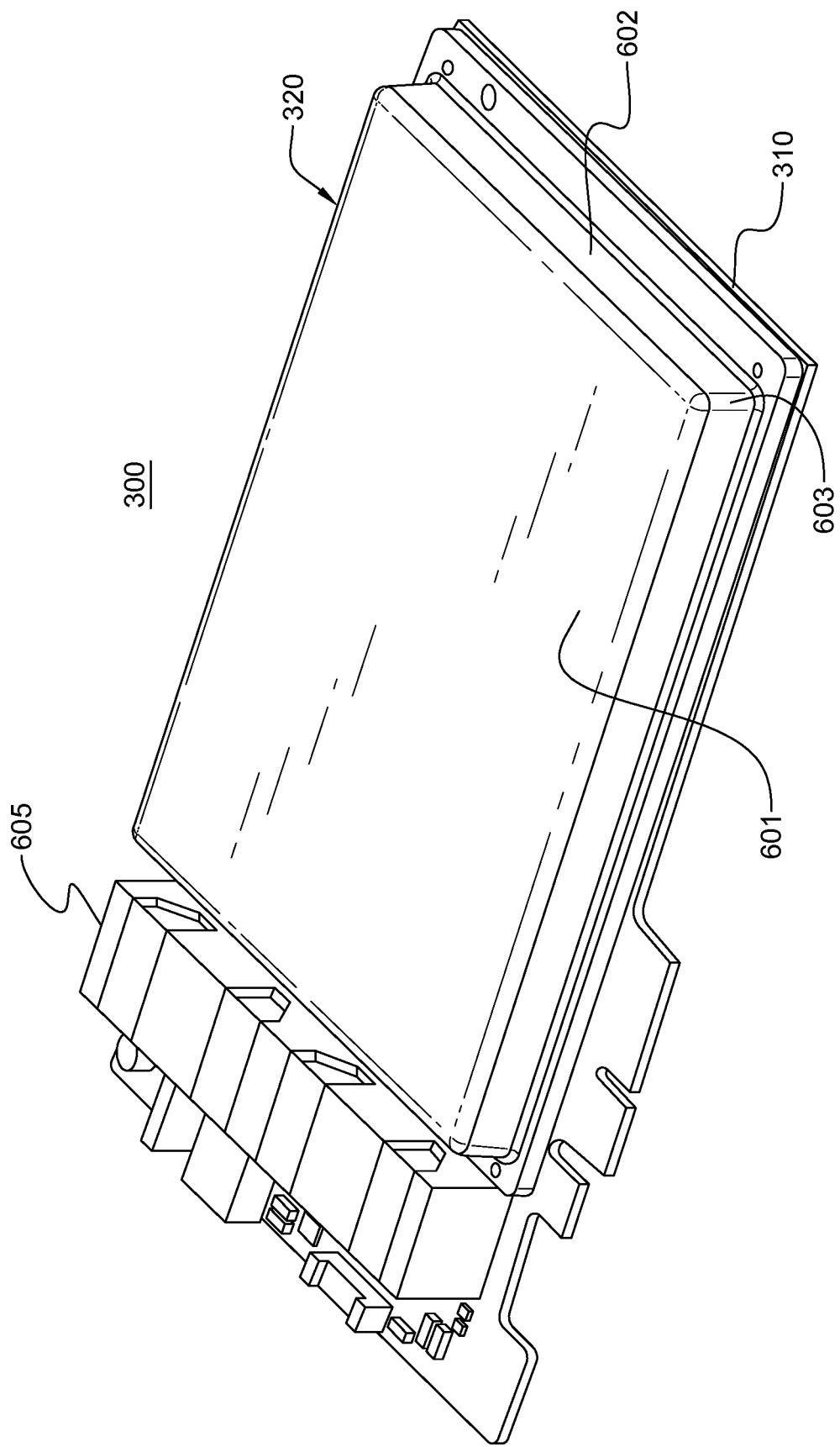
FIG. 6 is an isometric view of one embodiment of a tamper-respondent assembly, in accordance with one or more aspects of the present invention.

By way of further example, an isometric view of one embodiment of a tamper-proof electronic package 300 is depicted in FIG. 6, wherein an enclosure 320 is shown sealed to multilayer circuit board 310 to define a secure volume about one or more electronic components, as described herein. In the embodiment depicted, enclosure 320 may be formed of a thermally conductive material, and includes a main surface 601 and sidewall(s) 602 which include sidewall corners 603. An inner surface of enclosure 320 would include an inner main surface, and an inner sidewall surface corresponding to main surface 601 and sidewall(s) 602 respectively, with the inner main surface and inner sidewall surfaces being covered, at least in part, by one or more tamper-respondent sensors, such as described above. A power supply 605 or battery for the tamper-respondent sensor may be located, as depicted in this embodiment, external to the secure volume, with the tamper-respondent detector being configured to trip and destroy any protected or critical data if the power supply or battery is tampered with. Enclosure 320 may be adhered or mechanically affixed to multilayer circuit board 310, which as noted above, may include its own embedded tamper-respondent sensor(s).

Figure 7:
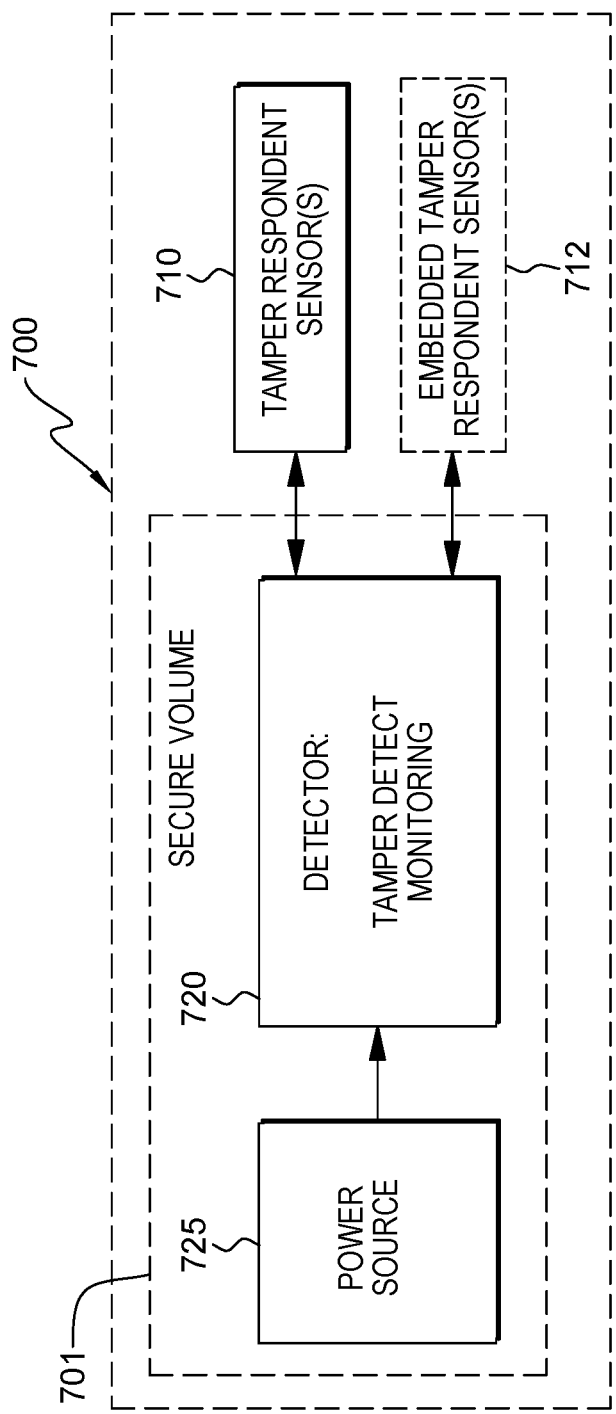
FIG. 7 is a schematic illustration of one embodiment of a tamper-respondent assembly which includes a detector for monitoring conductive lines of one or more tamper-detect networks of one or more tamper-respondent sensors of the tamper-respondent assembly, in accordance with one or more aspects of the present invention.

By way of example, FIG. 7 depicts one embodiment of a tamper-respondent assembly 700, which includes a secure volume 701 comprising one or more electronic components to be protected by one or more tamper-respondent sensors 710, and/or one or more embedded tamper-respondent sensors 712. Also provided within secure volume 701 is a detector 720 which monitors for a conductivity change due to a tamper event at one or more of the tamper-respondent sensors 710, 712. Power, in this example, may be provided by an embedded power source 725 provided within the secure volume 701 of tamper-respondent assembly 700. In one specific example, tamper-respondent assembly 700 may be a tamper-respondent assembly 300, such as described above in connection with FIGS. 3A-6, which includes a secure volume 301, tamper-respondent sensor 321, as well as embedded tamper-respondent sensors 400, 401, and detector 303.

By of way of further enhancement, disclosed herein with reference to FIGS. 8A-11B are various enhancements to electrical interconnect elements of or associated with one or more tamper-detect networks of one or more tamper-respondent sensors of a tamper-respondent assembly, such as described above. As noted, security solutions are desired to enhance physical protection of secure areas from undetected intrusion. Disclosed herein, in one or more aspects, are tamper-resistant interconnect elements, including both XY interconnect elements and Z axis interconnect elements (or interconnect vias) for enhancing defining a secure volume about, for instance, cryptographic devices and/or other electrical elements requiring a secure environment. In particular, advantageously disclosed herein are various x-axis, y-axis and/or z-axis interconnect elements and methods of fabrication that facilitate obscuring a circuit layout of the tamper-detect network(s) to make detection of the network or reverse engineering of the network by, for instance, x-ray inspection, visual inspection, metallographic cross-section, difficult to ascertain. By employing interconnect elements such as described herein in a single or a multilayer tamper-resistant circuitry, the physical protection of the secure volume enclosing the one or more electronic components to be protected may be significantly improved. Further, employing one or more aspects disclosed herein selectively can also improve tamper-resistance by enabling invisible programmable wiring.

Generally stated, in one or more embodiments, tamper-respondent assemblies and methods of fabrication are disclosed herein which include at least one tamper-respondent sensor, and a detector. The tamper-respondent sensor(s) includes: conductive lines forming, at least in part, at least one tamper-detect network of the tamper-respondent sensor (s); and at least one interconnect element associated with multiple conductive lines of the conductive lines forming, at least in part, at least one tamper-detect network. The at least one interconnect element includes at least one interconnect characteristic selected to facilitate obscuring a circuit layout of the at least one tamper-detect network. The detector monitors the at least one tamper-detect network of the tamper-respondent sensor(s) for a tamper event.

By way of example, the at least one interconnect characteristic may include an interconnect material that is undetectable by x-ray (i.e., by x-ray analysis). The at least one interconnect element may be formed of the interconnect material. Further, the conductive lines may be formed of a conductive material, with the conductive material and interconnect material being different materials. Still further, the conductive material may be detectably by x-ray. For example, the conductive material of the conductive lines may be a metal or metal alloy, and the interconnect material may be a nickel-phosphorus (NiP) or nickel-chromium (NiCr), such as the above-noted Omega-Ply® or Ticer™ products. Alternatively, the interconnect material could be formed of any sufficiently conductive material which is also undetectable by x-ray. For instance, the interconnect material could be carbon ink.

In one or more embodiments, the at least one interconnect element may include an interconnect via electrically connecting multiple conductive lines disposed on at least two different surfaces of the at least one tamper-respondent sensor. In the case of one or more interconnect vias, the at least one interconnect characteristic may include forming the interconnect via with an electrical interconnect material on a wall of the via with a thickness such that the interconnect via is difficult to detect, for instance, by x-ray. For example, the interconnect material on the wall of the via could be an electroless seed layer, a graphite seed layer, or a sputtered interconnect material. The thickness of the electrical interconnect material on the wall of the via may be chosen to balance conductivity of the material with its detectability, whether visual, x-ray or metallographic cross section.

In one or more implementations, an electrical characteristic of the at least one interconnect characteristic may include an electrical open circuit that defines an open interconnect element. The open interconnect element is a fictitious interconnect element which facilitates obscuring the circuit layout of the at least one tamper-detect network.

In one or more embodiments, the at least one tamper-respondent sensor may include at least one layer, and different conductive lines of the conductive lines may be disposed on different surfaces of the at least one layer. Further, the at least one interconnect element may include multiple interconnect vias between the different conductive lines disposed on the different surfaces. In one or more embodiments, an interconnect via of the multiple interconnect vias may be undetectable by x-ray analysis. Further, another interconnect via of the multiple interconnect vias may be a fictitious interconnect via not electrically connecting two or more different conductive lines. For instance, the interconnect via and the other interconnect via may be formed of different interconnect materials. Further, the other interconnect via may be detectable by x-ray, appearing on an x-ray analysis to be an actual electrical interconnect via within the circuit layout.

In one or more embodiments, an interconnect element of the at least one interconnect element may be an open circuited interconnect element, such that the interconnect element is a fictitious interconnect element which facilitates obscuring the circuit layout of the at least one tamper-detect network. For example, the open circuited interconnect element may include a difficult to detect, annular opening in a pad about an interconnect via, which open circuits electrical connection to the interconnect via.

In one or more particular examples described herein, a tamper-resistant secure enclosure is provided, for instance, for a cryptographic device, such as cryptographic processor. A tamper-detection sensor is disclosed which may include a combination of interconnect vias or interconnect technologies which are characterized by difficult to determine continuity (e.g., by x-ray inspection, visual inspection or metallographic cross-section). The interconnect via technologies may be selected from carbon filled vias, electroless seed layer only vias, graphite coated only vias, vias with thin sputtered coating only interconnect layers, laser drilled vias with depth controlled leaving thin insulating layer to eliminate electrical continuity, mechanical drilled vias with depths control leaving the thin insulating layer to create opening, and vias with sputtered insulation coating on the base and/or sidewalls to eliminate continuity.

Figure 8A:
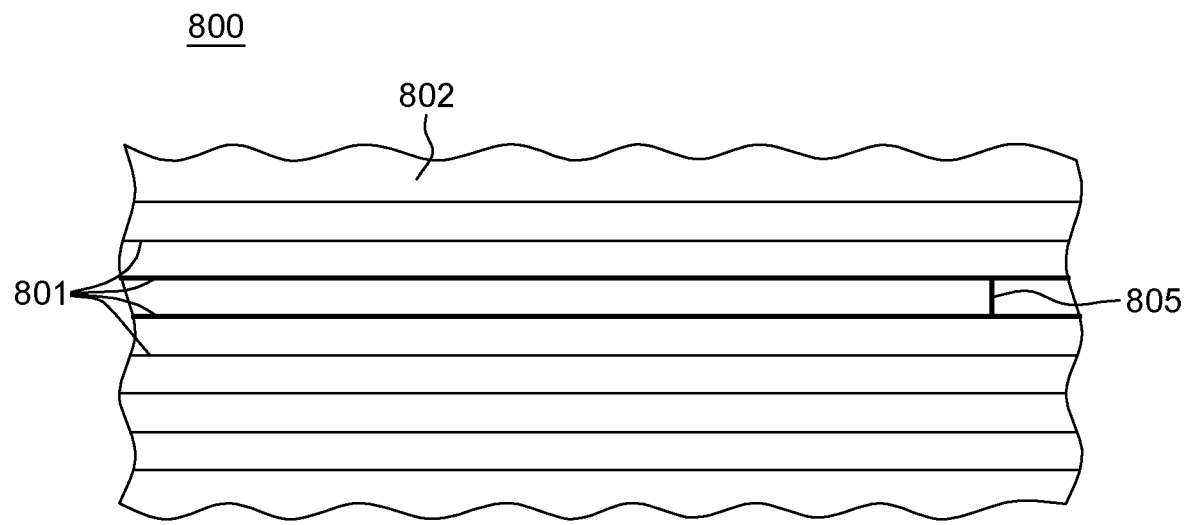
FIG. 8A is a plan view of one embodiment of conductive lines (shown exposed) of a tamper-respondent sensor which form, at least in part, at least one tamper-detect network, in accordance with one or more aspects of the present invention.
Figure 8B:
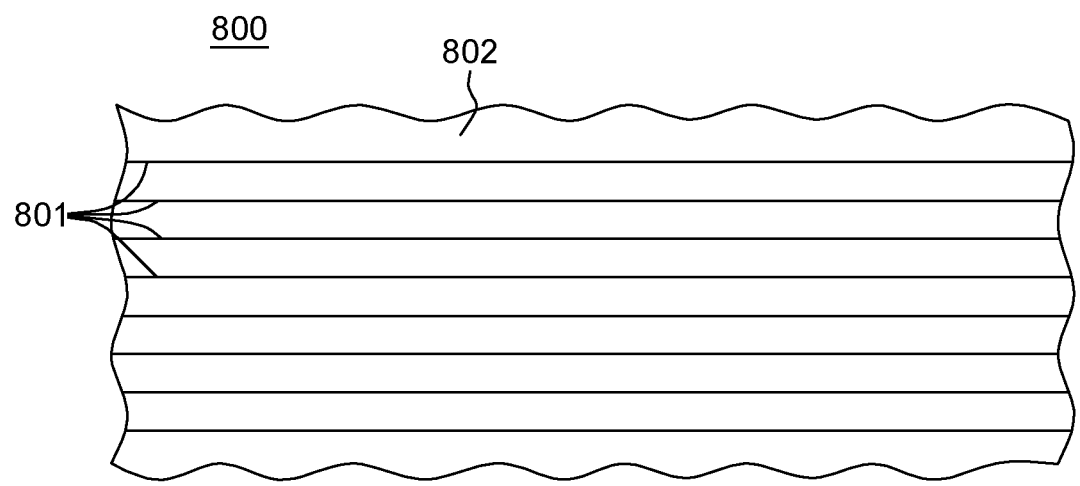
FIG. 8B depicts one embodiment of an x-ray image of the circuit lines of FIG. 8A (unexposed), wherein the interconnect element(s) has an interconnect characteristic which makes the interconnect element(s) undetectable by x-ray to obscure a circuit layout of the at least one tamper-detect network, in accordance with one or more aspects of the present invention.

FIGS. 8A & 8B depict one embodiment of a portion of a tamper-respondent sensor 800, in accordance with one or more aspects of the present invention. As illustrated, tamper-respondent sensor 800 may include multiple conductive lines 801 disposed on a surface 802 of a layer, such as a flexible layer of the tamper-respondent sensor. Note in this regard that conductive lines 801 and layer 802 may be the same or similar to the conductive lines and layers described above in connection with FIGS. 2A-2D. In the implementation of FIG. 8A, an XY interconnect element 805 is shown electrically interconnecting two conductive lines 801 of the tamper-respondent sensor such that the interconnect element 805 forms a portion of the tamper-detect network(s) of the tamper-respondent sensor. This can be seen visually in FIG. 8A, where the circuit lines are shown exposed for purpose of illustration, that is, with the outer protective covering layer or material not shown.

As shown in FIG. 8B, which is an x-ray depiction of the structure of FIG. 8A with the outer protective layer over the conductive lines in place, the interconnect element 805 of FIG. 8A is undetectable. This can be accomplished by selecting the interconnect material forming interconnect element 805 of FIG. 8A to be x-ray undetectable. For instance, in one or more implementations, the conductive lines 801 could be formed of an x-ray detectable metal or metal alloy, such as copper traces, which are easy to detect, and the interconnect element could be formed of an interconnect material that is impossible to detect through x-ray analysis. For instance, the interconnect material of the interconnect element 805 could be a resistive material, such as carbon ink, or the above-noted Omega-Ply™, Ticer™, as well as any other materials that may be sufficiently electrically conductive, but otherwise undetectable by x-ray analysis. When a tamper event is attempted by, for instance, reverse engineering the tamper-detect network to bypass the protection security by shunting the conductive lines, it would be difficult to know which conductive lines or traces are electrically interconnected since the interconnect element(s) is undetectable by x-ray analysis.

Figure 9A:
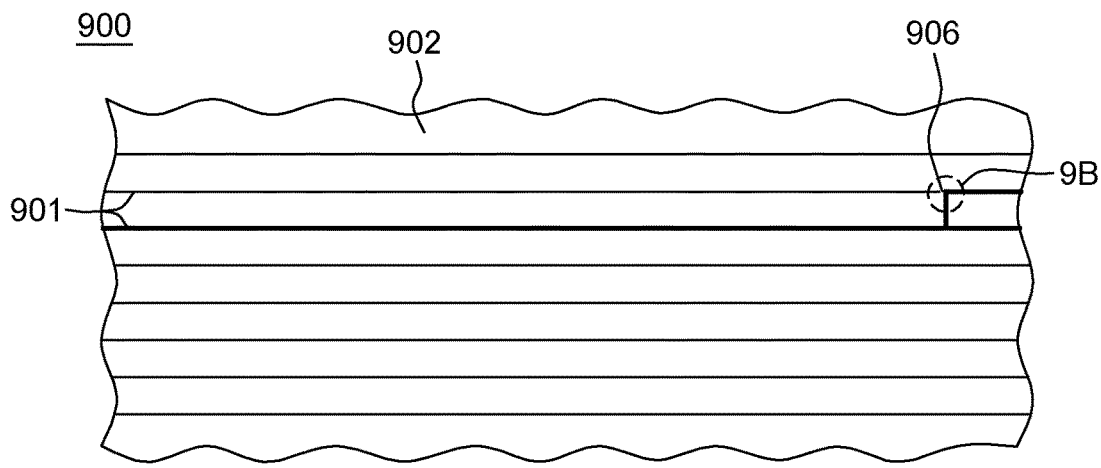
FIG. 9A depicts another embodiment of circuit lines (shown exposed) of a tamper-respondent sensor which facilitate defining at least one tamper-detect network and which include one or more interconnect elements with a characteristic(s) which obscures a circuit layout of the at least one tamper-detect network, in accordance with one or more aspects of the present invention.
Figure 9B:
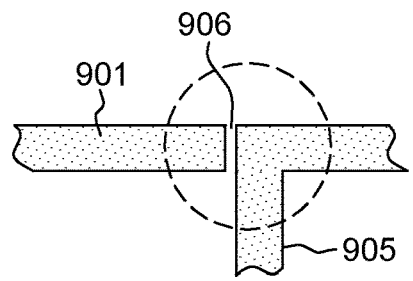
FIG. 9B is a partial enlarged view of a portion of the circuit lines of FIG. 9A, showing a narrow open circuit of a circuit line associated with the interconnect element to facilitate obscuring the circuit layout, in accordance with one or more aspects of the present invention.

FIGS. 9A & 9B depict a further example of an XY interconnect element with an associated interconnect characteristic that facilitates obscuring a circuit layout of the tamper-detect network. As illustrated in FIG. 9A, a tamper-respondent sensor 900 may include conductive lines 901 on a layer 902 of the sensor, which may be the same or similar to the lines and layers described above, such as in connection with FIGS. 2A-2D. An interconnect element 905 is provided which electrically interconnects two or more conductive lines 901 of the tamper-detect network of the tamper-respondent sensor. In this embodiment, the interconnect element 905 has associated therewith a thin open circuit 906, which may be either part of the interconnect element 905 itself or adjacent to the interconnect element in one of the conductive lines to which the interconnect element connects. In the embodiment of FIG. 9B, the open circuit 906 is shown in the conductive line 901, where the interconnect element connects to the line. This open circuit may be provided to further obscure the nature of the circuit layout of the tamper-detect network. As specific examples, one or more narrow openings may be formed in or near one or more interconnect elements (i.e., electrical shorts) in the conductive lines, such as in copper or resistant traces. The opening has a width characterized by a distance sufficient to establish the electrical opening, but difficult to detect by inspection of the tamper-detect network, such as by x-ray or visual inspection, or by metallographic cross section. By way of example, the width of the opening could be 5 µm or less, such as in a range of 0.1 µm to 5 µm.

FIGS. 10A-10D depict examples of z-axis interconnect elements, also referred to herein as interconnect vias. As shown in FIG. 10, a tamper-respondent sensor 1000 may include conductive lines 1001 disposed on a surface of one or more layers 1002, and conductive lines 1003 disposed on another surface of layer(s) 1002. Those skilled in the art will note that, as with the above embodiments, conductive lines 1001, 1003, and layer(s) 1002 may be the same or similar to the conductive lines and layers described above, such as in connection with FIGS. 2A-2D.

Figure 10A:
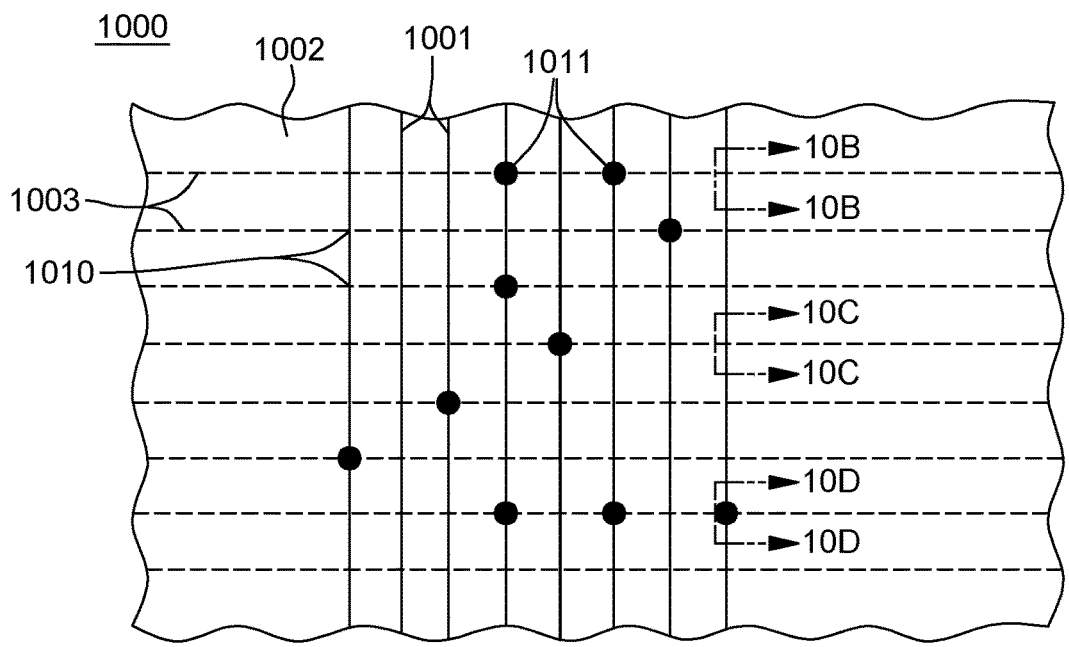
FIG. 10A depicts one embodiment of circuit lines of a tamper-respondent sensor comprising multiple conductive lines on different surfaces of the sensor, and depicting multiple interconnect elements which include one or more characteristics selected to obscure circuit layout of a tamper-detect network(s) of the tamper-respondent sensor, in accordance with one or more aspects of the present invention.

As illustrated in FIG. 10A, in the embodiment depicted, conductive lines 1001 cross over underlying conductive lines 1003 such that any one of a plurality of cross-point connections are possible. In one or more embodiments, FIG. 10A may be an example of an x-ray representation of a portion of the tamper-detect network of the tamper-respondent sensor 1000. As illustrated by this representation, a number of cross-points 1010 have no discernable interconnect vias associated therewith, to connect in the z direction respective conductive lines 1001 and 1003, while other cross-points 1011 have what appear to be interconnect vias associated therewith. However, in accordance with one or more aspects of the present invention, any one of the cross-points may actually be electrically connecting between conductive lines 1001 and 1003 with the presence 1011 or absence 1010 of interconnect vias in an x-ray imaging of the tamper-detect network being non-determinative of the actual circuit layout of the tamper-detect network. In particular, as explained below with reference to FIGS. 10B-10D, the z-axis connection between conductive lines on different layers or surfaces may be difficult, if not impossible, to determine fully.

Figure 10B:
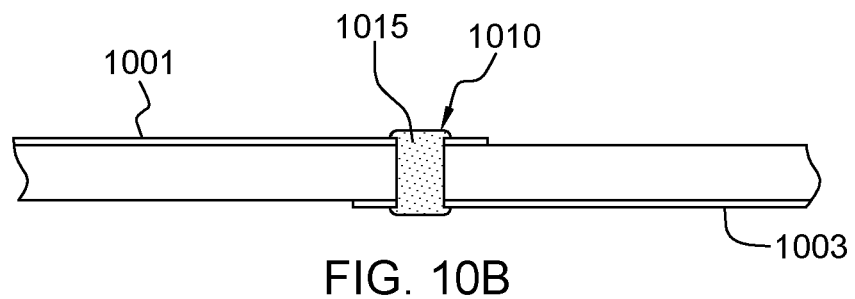
FIG. 10B is a partial elevational view of one embodiment of the tamper-respondent sensor of FIG. 10A, taken through line 10B-10B thereof, in accordance with one or more aspects of the present invention.

By way of example, FIG. 10B is an exemplary cross-sectional elevational view of one embodiment of the tamper-respondent sensor 1000 of FIG. 10A taken along line 10B-10B thereof. In this embodiment, the cross-point 1010, which appears in the x-ray analysis of FIG. 10A do not include a z-axis connection, actually includes a z-axis connection, or interconnect via, 1015 which electrically connects a respective conductive line 1001 on the upper surface of the layer with a respective conductive line 1003 on a lower surface of the layer. By way of example, the interconnect via 1015 may be formed of an interconnect material that is undetectable by x-ray. For instance, the interconnect material could be a resistive material that is x-ray undetectable, such as carbon ink, a nickel-phosphorous (NiP) material, or a nickel-chromium (NiCr) material. By way of example, in one or more implementations, the conductive lines 1001, 1003 may be formed of a conductive material that is x-ray detectable, which in combination with the interconnect material 1015 that is x-ray undetectable, makes the z-axis interconnections, and therefore, the circuit layout, difficult to determine. In one or more embodiments, the interconnect material 1015 could comprise carbon ink that is screen filled.

Figure 10C:
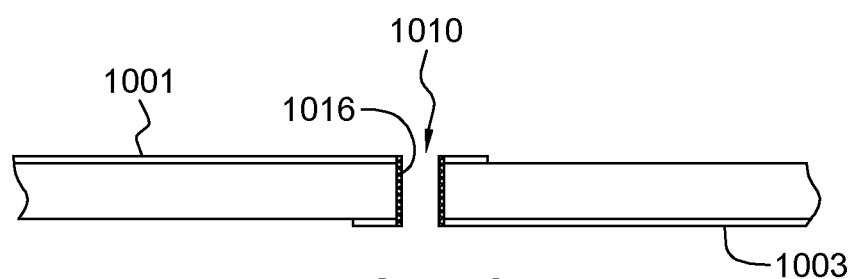
FIG. 10C depicts a partial elevational view of one embodiment of the tamper-respondent sensor of FIG. 10A, taken through line 10C-10C thereof, in accordance with one or more aspects of the present invention.

FIG. 10C depicts another embodiment of a cross-point connection 1010 which has an interconnect characteristic making the cross-point connection difficult to detect by x-ray. In this example, the cross-point characteristic used is that the interconnect element 1016 is defined with a thickness on a wall on the via at the cross-point location that is difficult to detect by x-ray. For instance, in one or more implementations, the interconnect element may comprise an electroless seed layer, or a graphite seed layer, or other sputter interconnect material, with an interconnect characteristic of a minimal material thickness on the wall of a via. For instance, the thickness of the material on the wall of the via could be 5 µm or less, such as a material thickness in the range of 0.1 µm to 5 µm. As a further example, any conductive or resistive seed layer could be employed, to provide a thin essentially conductive monolayer of material, such as a metal, metal alloy, carbon, etc. In this implementation, the interconnect thickness is so thin that the interconnection is essentially undetectable visually or with x-ray analysis.

Figure 10D:
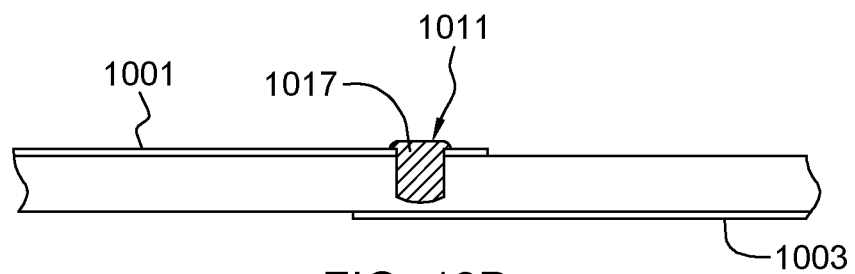
FIG. 10D is a partial elevational view of one embodiment of the tamper-respondent sensor of FIG. 10A, taken through line 10D-10D thereof, in accordance with one or more aspects of the present invention.

In FIG. 10D, taken along line 10D-10D of FIG. 10A, an apparent Z-axis interconnect or interconnect via 1011 is shown in the x-ray analysis of FIG. 10A, but in the cross sectional elevational view of 10D, it is shown to actually be an open circuited interconnect via. In this example, the interconnect via is assumed to include an interconnect material 1017 that is x-ray detectable, such as a metal or metal alloy (e.g., a copper via), so that the interconnect appears to be an actual electrical interconnect in the z-axis direction at the cross point between respective conductive lines 1001, 1003, but in reality, the interconnect via does not extend all the way through layer 1002, which is, in one or more embodiments, a flexible non-conductive layer. For instance, layer 1002 may be a polymer material, such as described above in connection with FIGS. 2A-2D. The result is that the particular interconnect via 1011 in FIG. 10D is actually a fictitious interconnect via, which renders ascertaining of the actual circuit layout more difficult to detect during a tamper event.

Advantageously, by mixing combinations of detectable interconnect vias, actual, but undetectable interconnect vias, and detectable but fictitious interconnect vias, the actual circuit layout of the tamper-detect network may be obscured, rendering it significantly more difficult to tamper through undetected by the tamper-respondent assembly.

Figure 11A:
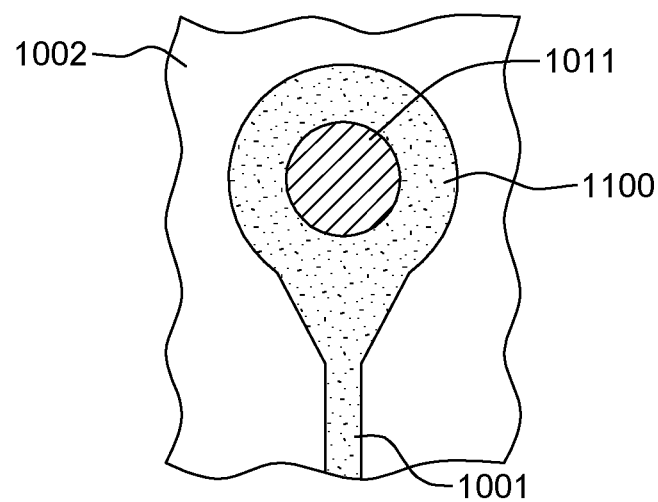
FIG. 11A is a plan view of one embodiment of an interconnect via and surrounding capture pad to be modified, in accordance with one or more aspects of the present invention.
Figure 11B:
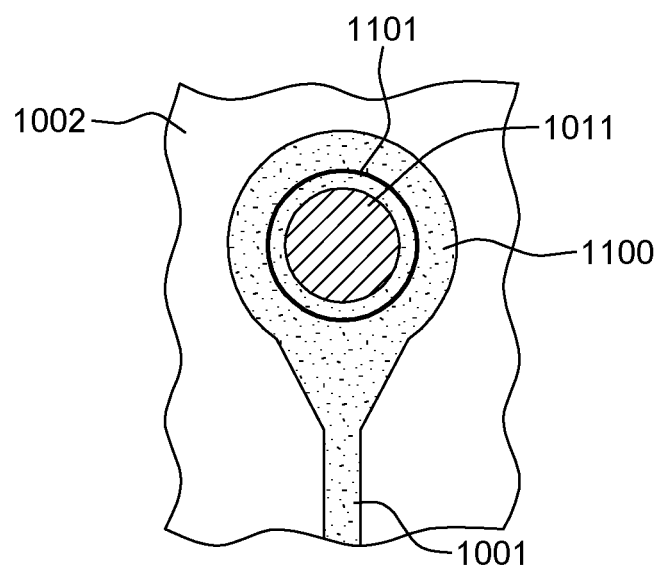
FIG. 11B depicts the structure of FIG. 11A with an narrow annular opening formed about the interconnect via in the capture pad to open circuit connection to the interconnect via, in accordance with one or more aspects of the present invention.

FIGS. 11A & 11B depict a further example of a fictitious interconnect via, in accordance with one or more aspects of the present invention. As illustrated in FIG. 11A, an x-ray detectable interconnect via 1011 through a layer 1002 may have surrounding on one surface an electrical capture pad 1100 which facilitates electrical connection of the interconnect via 1011 to a conductive line 1001 (in this example). As illustrated in FIG. 11B, a thin annular open ring 1101 may be provided to electrically open circuit the interconnect via 1001 connection to conductive line 1001. The result is that there is no electrical connection through this interconnect via between different conductive lines on different surfaces or layers of the tamper-respondent sensor. By making the annular ring sufficiently small, it is possible to define the open circuit around interconnect via 1011, without making the open circuit nature of the connection easy to identify. For instance, the annular ring gap may be a distance of 5 µm or less, such as a distance in a range of 0.1 µm to 5 µm.

Advantageously, disclosed herein with reference to FIGS. 8A-11B are various configurations of interconnect elements with interconnect characteristics associated therewith making the circuit layout of the tamper-detect network difficult to detect. It is possible to provide a mixture of physical design points within the same physical footprint using the configurations disclosed. For instance, all tamper-detect networks of a sensor need not have the same wiring pattern, and it is possible to make actual connections invisible to x-ray analysis, as well as make them programmable to allow for multiple patterns or unique patterns, identified such as by serial number of a particular tamper-respondent assembly implementation. The configuration provided facilitate increasing complexity of an attempted reverse engineer, thereby enhancing detection capability of the tamper-respondent assembly. Further, testing techniques to attempt the tamper of the package become significantly more complex as well.

Disclosed herein in one or more implementations are, for instance, interconnect element technologies or approaches that make actual circuit layout difficult to detect, for instance, by making it hard to detect whether two or more lines are electrically connected. For instance, hard to detect resistive connections between easy to detect metal traces, such as copper traces, may be provided. Further narrow openings in conductive layers may be provided, such as near electrical elements creating shorts between conductive lines. Further, narrow openings may be provided such as annular rings in the capture pad about an interconnect via. As noted, multiple invisible programmable design points may be employed within a particular tamper-detect network design in order to improve tamper-resistance.

Further, interconnect vias, or Z-axis interconnects, may utilize various different technologies to make it difficult to detect whether a particular cross-point has electrical connection continuity between conductive lines on different surfaces of the tamper-respondent sensor. By way of example, carbon filled vias, electroless seed layer only vias, graphite coated only vias, vias with thin sputtered coating only interconnect vias may all be provided. Further, laser drilled vias with depth controlled leaving a thin insulating layer may be utilized which eliminates continuity, that is, open circuits the electrical interconnect via. Further, mechanical drilled vias may be provided again with depth control leaving a thin insulating layer to create an open circuit in the interconnect via may be provided. Also, vias may be sputtered with insulation coating on a base of the via and/or on sidewalls of the vias to eliminate continuity between different conductive lines on different surfaces of the sensor, notwithstanding the apparent presence of the interconnect via in the tamper-detect network.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A tamper-respondent assembly comprising:
   at least one tamper-respondent sensor including:
      conductive lines forming, at least in part, at least one tamper-detect network of the at least one tamper-respondent sensor; and
      at least one interconnect element associated with multiple conductive lines of the conductive lines forming, at least in part, the at least one tamper-detect network, the at least one interconnect element comprising at least one interconnect characteristic selected to facilitate obscuring a circuit layout of the at least one tamper-detect network;

a detector to monitor the at least one tamper-detect network of the at least one tamper-respondent sensor for a tamper event; and wherein:

the at least one tamper-respondent sensor comprises at least one layer, and different conductive lines of the conductive lines are disposed on different surfaces of the at least one layer, and the at least one interconnect element comprises multiple interconnect vias between the different conductive lines disposed on the different surfaces;

an interconnect via of the multiple interconnect vias is undetectable via x-ray analysis;

an other interconnect via of the multiple interconnect vias comprises a fictitious interconnect via not electrically connecting two or more different conductive lines;

the interconnect via and the other interconnect via are formed of different interconnect materials; and the other interconnect via is detectable by x-ray, appearing in x-ray analysis to be an actual electrical interconnect via.

2. The tamper-respondent assembly of claim 1, wherein the conductive lines are formed of a conductive material, the conductive material and the interconnect material being different materials.

3. The tamper-respondent assembly of claim 2, wherein the conductive material is detectable by x-ray.

4. The tamper-respondent assembly of claim 1, wherein the interconnect via comprises an electrical interconnect material on a wall of the interconnect via with a thickness making the interconnect via difficult to detect by x-ray.

5. The tamper-respondent assembly of claim 4, wherein the electrical interconnect material is selected from a group consisting of an electroless seed layer, a graphite seed layer or a sputtered interconnect material.

6. A tamper-respondent assembly comprising:

at least one electronic component;

an enclosure surrounding, at least in part, the at least one electronic component;

at least one tamper-respondent sensor associated with the enclosure and facilitating defining a secure volume about the at least one electronic component, the at least one tamper-respondent sensor including:

conductive lines forming, at least in part, at least one tamper-detect network of the at least one tamper-respondent sensor; and at least one interconnect element associated with one or more conductive lines of the conductive lines forming, at least in part, the at least one tamper-detect network, the at least one interconnect element comprising at least one interconnect characteristic selected to facilitate obscuring a circuit layout of the at least one tamper-detect network;

a detector to monitor the at least one tamper-detect network of the at least one tamper-respondent sensor for a tamper event; and wherein:

the at least one tamper-respondent sensor comprises at least one layer, and different conductive lines of the conductive lines are disposed on different surfaces of the at least one layer, and the at least one interconnect element comprises multiple interconnect vias between the different conductive lines disposed on the different surfaces;

an interconnect via of the multiple interconnect vias is undetectable via x-ray analysis;

an other interconnect via of the multiple interconnect vias comprises a fictitious interconnect via not electrically connecting two or more different conductive lines;

the interconnect via and the other interconnect via are formed of different interconnect materials; and the other interconnect via is detectable by x-ray, appearing in x-ray analysis to be an actual electrical interconnect via.

\* \* \* \* \*